(12) United States Patent
Nowicky

(10) Patent No.: US 7,795,434 B2
(45) Date of Patent: Sep. 14, 2010

(54) QUATERNARY CHELIDONINE AND ALKALOID DERIVATIVES, PROCESS FOR THEIR PREPARATION AND THEIR USE IN MANUFACTURE OF MEDICAMENTS

(76) Inventor: Wassyl Nowicky, Margaretenstrasse 7, A-1040, Vienna (AT)

( * ) Notice: Subject to any disclaimer, the term of this patent is extended or adjusted under 35 U.S.C. 154(b) by 790 days.

(21) Appl. No.: 10/549,433

(22) PCT Filed: Mar. 12, 2004

(86) PCT No.: PCT/EP2004/002637
§ 371 (c)(1),
(2), (4) Date: Oct. 17, 2005

(87) PCT Pub. No.: WO2004/082698
PCT Pub. Date: Sep. 30, 2004

(65) Prior Publication Data
US 2006/0154947 A1    Jul. 13, 2006

(30) Foreign Application Priority Data
Mar. 18, 2003    (EP) .................................. 03006015

(51) Int. Cl.
C07D 491/12    (2006.01)
A61K 31/4741    (2006.01)
(52) U.S. Cl. ........................................ 546/41; 514/279
(58) Field of Classification Search .................. 514/279; 546/41
See application file for complete search history.

(56) References Cited

U.S. PATENT DOCUMENTS

| 3,865,830 | A | 2/1975 | Turkevich et al. |
| 4,970,212 | A | 11/1990 | Nowicky |
| 5,981,512 | A | 11/1999 | Nowicky |

FOREIGN PATENT DOCUMENTS

| AT | 354 644 | 1/1980 |
| AT | 377 988 | 5/1985 |
| DE | 2 028 330 | 5/1971 |
| FR | 2 366 020 | 4/1978 |
| GB | 1 304 064 | 1/1973 |
| GB | 1304064 | 1/1973 |
| GB | 2110533 | 6/1993 |
| WO | WO 01/70203 | 9/2001 |
| WO | WO 03/041721 | 5/2003 |

OTHER PUBLICATIONS

Zbierska, J. et al.: Anticancer and antibiotic properties of N-methylchelidonine methyl sulfate. Herba polonica, vol. 25, pp. 311-316, 1979.*
Database Chemical Abstracts Online! Database accession No. 1982:173909, abstract, XP002239900 & Zhao Y. et al.: "Studies on the antimalarial activity of protopine derivatives" Chinese Pharmaceutical Bulletin (Yaoxue Tongbao), vol. 16, No. 6, Jun. 1981, pp. 7-10, XP001147793 ISSN: 0512:7343.
Tanaka S. et al.: "Influence of natural and synthetic compounds on cell surface expression of cell adhesion molecules, ICAM-1 and VCAM-1" Planta Medica Thiem, Stuttgart, DE, vol. 67, No. 2, 2001, pp. 108-113, XP009003131 ISSN: 0032-0943.
Schmeller T., et al.: "Biochemical activities of berberine, palmatine and sanguinarine mediating chemical defence against microorganisms and herbivores" Phytochemistry, Pergamon Press, GB, vol. 44, No. 2, Jan. 1997, pp. 257-266, XP004292781 ISSN: 0031-9422.
Schlotterbeck J.O., et al.: "Beiträge zur Chemie des stylophorum diphyllum", Chemische Berichte, vol. 35, 1902, pp. 7-23, XP009009873 ISSN: 0009-2940.
Henschke A.: "I. Über das Cheldonin" Archiv Der Pharmacie, vol. 226, 1888, pp. 624-644, XP009009872 ISSN: 0365-6233.
Walzterova D., et al.: "Inhibition of liver alanine aminotransferase activity by some benzophenanthridine alkaloids", Journal of Medicinal Chemistry, vol. 24, No. 9, Sep. 1981, pp. 1100-1103, XP002239893 ISSN: 0022-2623.
Ishii H., et al.: "Studies on the chemical constituents of rutaceous plants. LX. Development of a versatile method for syntheses of the antitumour benzo[c]phenanthridine alkaloids. 9. Efficient syntheses and antitumuor activties of nitidine and related non-phenolic benzo[c]phenanthrdine alkaloids", Chemical and Pharmaceutical Bulletin, vol. 33, No. 10, 1985, pp. 419-4151, XP001147415 ISSN: 0009-2363.
Lombardini J.B., et al.: "Effects of benzophenanthridine alkaloids on the phosphorylation of an approx 44 kDa protein present in a mitochondrial fraction of the rat heart", Biochemical Pharmacology, vol. 51, No. 2, Jan. 26, 1996, pp. 151-157, XP002239894 ISSN: 0006-2952.
Nakanishi T., et al.: "Structural considerations of NK109, an antitumour benzo[c]phenanthridine alkaloid", Journal of Natural Products, vol. 62, No. 6, Jun. 1999, pp. 864-867, XP002239895 ISSN: 0163-3864.
Valpuesta M., et al.: "From protopines to berbines: synthesis of 1-methoxystylopine and its N-metho salts from coulteropine", Tetrahedron, Elsevier Science Publishers, Amsterdam, NL, vol. 58, No. 25, Jun. 17, 2002, pp. 5053-5059, XP004366428 ISSN: 0040-4020.
Slavik J., et al.: "Quaternary alkaloids from the roots of Argemone platyceras LINK et Otto", Collection of Czechoslovak Chemical Communications, vol. 41, 1976, pp. 285-289, XP009009913 ISSN: 0010-0765.

(Continued)

Primary Examiner—Charanjit S Aulakh
(74) Attorney, Agent, or Firm—Ostrolenk Faber LLP

(57) ABSTRACT

Alkaloid reaction products obtainable in a process wherein alkaloids are reacted with an alkylating agent, preferably thiotepa, whereafter unreacted alkylating agent and other water-soluble compounds are removed from the reaction mixture by washing with water or a suitable aqueous solvent, whereafter the reaction mixture is subjected to a treatment with strong acid, preferably hydrogen chloride (HCl), to precipitate a water soluble salt of the reaction products. The precipitated reaction products comprise at least one quaternary alkaloid derivative and are suitable as drugs for prophylactic or therapeutic application, particularly in the treatment of immunological or metabolic dysfunctions, and cancer.

17 Claims, 11 Drawing Sheets

OTHER PUBLICATIONS

Schmidt E. "46. Über Paveraceen-Alkaloïde", *Archiv Der Pharmacie*, vol. 231, 1893, pp. 168-183, XP009009914 ISSN: 0365-6233.

Takao N., et al.: "Studien üiber die Alkaloide de Pavaveraceen. Die Alkaloide von Corydalis incisa(10). Über die struktur des (+)-14-Epicorynolins", *Chemical and Pharmaceutical Bulletin*, vol. 21, 1973, pp. 1096-1102, XP009009871 ISSN: 0009-2363.

Danckwortt, P.W.: "Zur Kenntnis des Protopins and Kyrptopins", *Archiv Der Pharmacie*, vol. 250, 1912, pp. 590-646, XP00900915 ISSN: 0365-6233.

Manske R.H.F., et al.: "The alkaloids of papaveraceous plants. XXIV. Hunnemannia fumariaefolia Sweet and the constitution of a new alkaloid, hunnemanine", *Journal of the American Chemical Society*, vol. 64, No. 7, Jul. 1942 pp. 1659-1661, XP002239896 ISSN: 0002-7863.

Redemann C.E. et al.: "Characterisation of certain alkaloids from Fagara coco" *Journal of the American Chemical Society*, vol. 71, No. 3, Mar. 19, 1949, pp. 1030-1034, XP002239897 ISSN: 0002-7863.

Ulrichova J., et al.: "Cytotoxicity of natural compounds in hepatocyte cell culture models. The case of quaternary benzo[c]phenanthridine alkaloids" *Toxicology Letters*, vol. 125, No. 1-3, Dec. 15, 2001, pp. 125-132, XP002239898 ISSN: 0378-4274.

Zhang G.L., et al.: "Alkaloids from Dactylicsnos torulosa" *Phytochemistry*, vol. 40, No. 1, 1995, pp. 299-305, XP002239899 ISSN: 0031-9422.

"Synthesis of Protopine. A Novel Conversation of the Proberberine Alkaloid Stylopine to a Tetrahydrodibenz[c,g]azecine Derivative", B. K. Kulkarni et al., Dept. of Chemistry, Centre for Basic Research, Hocchat India Limited, Mar.-Apr. 1990, vol. 27, pp. 623-627. Received Sep. 20, 1988.

Australian Search Report dated Sep. 7, 2007 corresponding to Australian Patent Application No. GCC/P/2004/3508.

Schlotterbeck J.O., et al.: "Beiträge zur Chemie des stylophorum diphyllum", *Chemische Berichte*, vol. 33, 1902, pp. 7-23, XP009009873 ISSN: 0009-2940.

Henschke A.: "I. Über das Cheldonin" *Archiv Der Pharmacie*, vol. 226, 1888, pp. 624-644, XP009009872 ISSN: 0365-6233.

\* cited by examiner

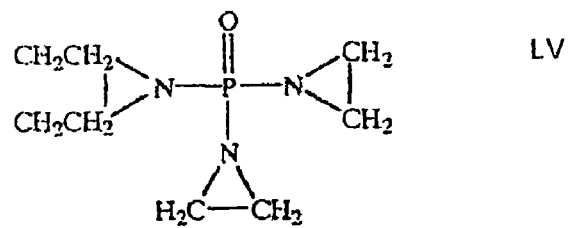 LV
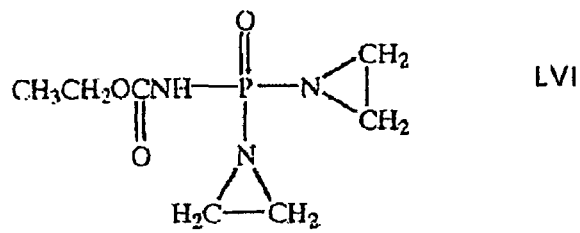 LVI
FIG. 3 (a)
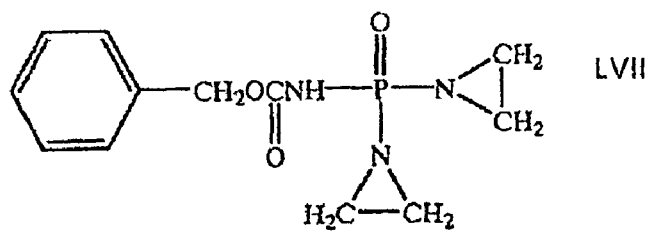 LVII
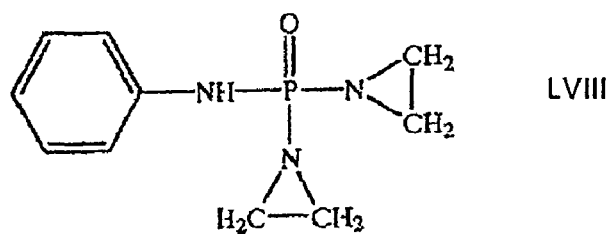 LVIII
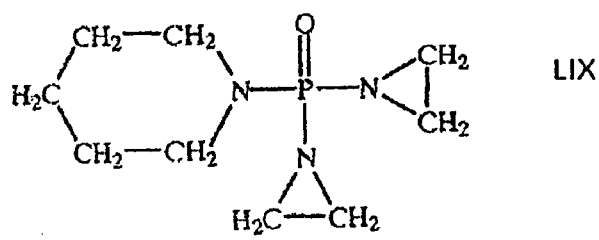 LIX
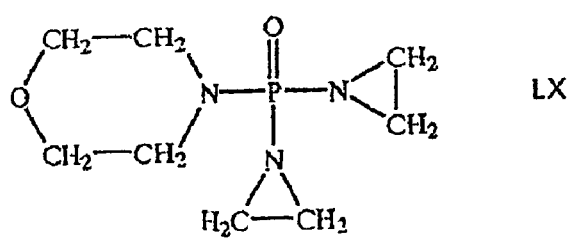 LX

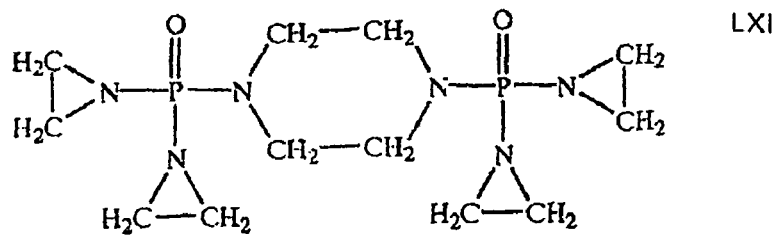 LXI
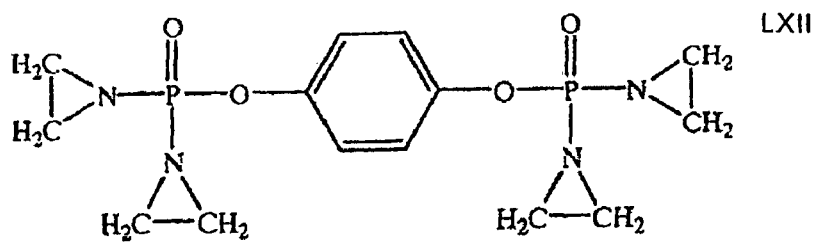 LXII
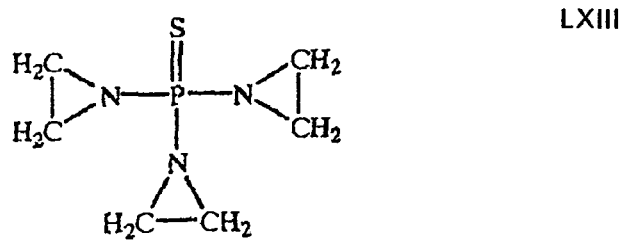 LXIII
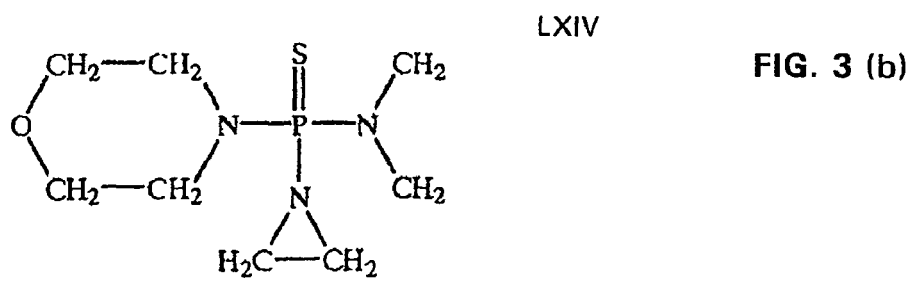 LXIV
FIG. 3 (b)
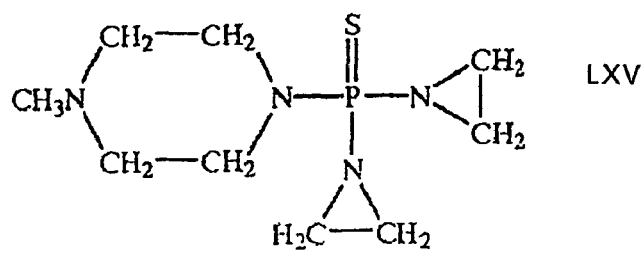 LXV
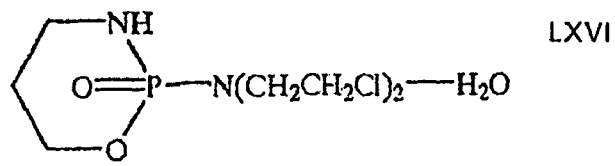 LXVI

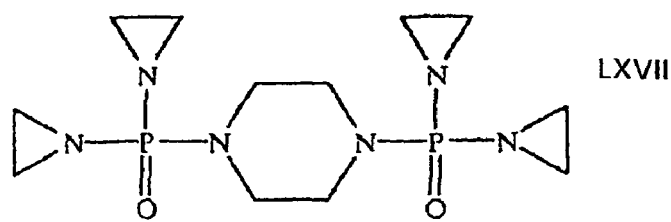
LXVII
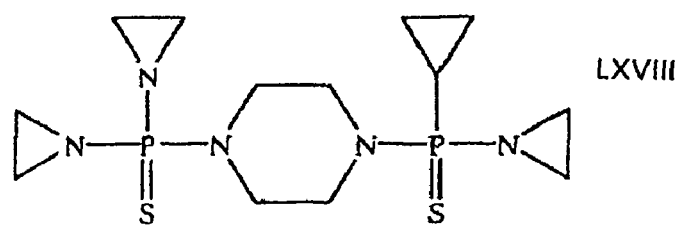
LXVIII
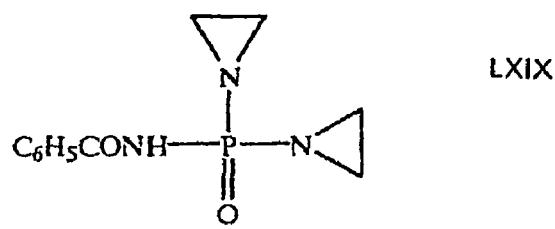
LXIX
FIG. 3 (c)
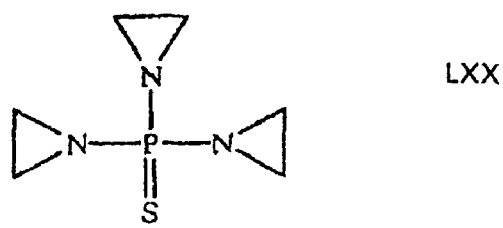
LXX
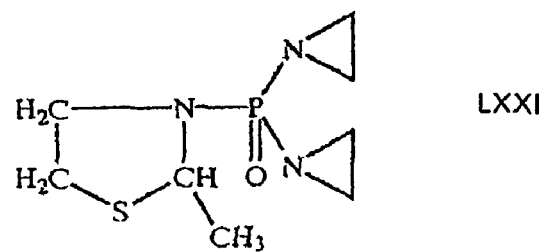
LXXI
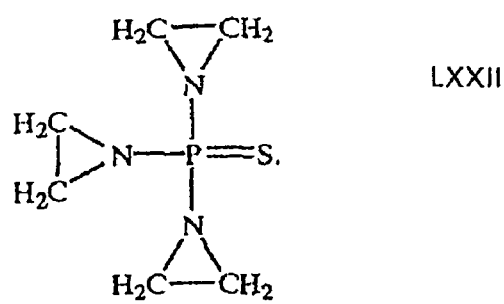
LXXII

US 7,795,434 B2

QUATERNARY CHELIDONINE AND ALKALOID DERIVATIVES, PROCESS FOR THEIR PREPARATION AND THEIR USE IN MANUFACTURE OF MEDICAMENTS

CROSS REFERENCE TO RELATED APPLICATION

The present application is a 35 U.S.C. §371 national phase conversion of PCT/EP2004/002637, filed Mar. 12, 2004, which claims priority of European Application No. 03006015.6 filed Mar. 18, 2003.

FIELD OF THE INVENTION

The present invention is in the field of drug development and health care and relates to the alkaloid chelidonine and derivatives thereof wherein the nitrogen in the chelidonine molecule is a quaternary nitrogen. The invention further relates to a method of manufacture of such compounds, to compositions containing such compounds and to applications thereof for the treatment of various diseases and bodily conditions.

STATE OF THE ART

The alkaloid chelidonine and compositions containing chelidonine are known in the art, as are therapeutic applications of chelidonine or some chelidonine derivatives in the treatment of various bodily conditions and diseases, including metabolic dysfunctions and tumours.

DE 2 028 330 and U.S. Pat. No. 3,865,830 disclose the preparation of thiophosphoramide-isoquinoline adducts by reacting selected alkaloids of *Chelidonium majus* L. with tris(1-aziridinyl)phosphine sulphide in an organic solvent.

AT 354 644 and AT 377 988 describe processes for the preparation of phosphorus derivatives of alkaloids by reaction with carcinostatic phosphorus compounds, which are provided in a water-soluble form by conversion into their salts. A disadvantage of the disclosed processes is that the conversion of the reaction products into a water-soluble salt is not complete and the predominant part of the reaction products remains water-insoluble.

U.S. Pat. No. 5,981,512 discloses the use of the substances disclosed in AT 377 988 and AT 354 644 for the treatment of radiation damage.

The compounds described in said patents have different cytostatic and carcinostatic activity. Mixtures of alkaloids, in particular of the total alkaloids of *Chelidonium majus* L., have proved therapeutically particularly promising, the pharmacological activity of which has been demonstrated in several studies on cancer treatment. Unreacted reagent is removed from the synthesis mixture following completion of the reaction. Since tris(1-aziridinyl)phosphine sulphide (hereinafter also referred to as "thiotepa") is soluble in organic solvents, such as benzene, ether or chloroform, it is proposed in the prior art methods to remove the unreacted tris(1-aziridinyl) phosphine sulphide from the synthesis mixture by washing the reaction products with ether.

While the aforementioned prior art methods for the manufacture of pharmacologically active chelidonine derivatives have in common that they require purification of the final product using inflammable or even explosive organic solvents, it was now found that the purification could also and with even better results be accomplished using an aqueous solvent.

BRIEF DESCRIPTION OF THE INVENTION

In one aspect the invention relates to a novel process for the preparation of a reaction product of alkaloids, particularly of chelidonine, oxychelidonine or methoxychelidonine, with suitable alkylating agents, which process involves at least one washing step with an aqueous solvent, preferably water, after completion of the alkylating reaction.

The process also comprises a step of converting the alkaloid derivatives into water-soluble salts, for making injectable pharmaceutical preparations of low toxicity and having a broad spectrum of therapeutic activity.

In another aspect the present invention relates to the water-soluble reaction products, e.g. comprising chelidonine derivatives, wherein the initially tertiary nitrogen in the alkaloid molecule has been converted into a quaternary nitrogen and wherein the fourth ligand to the quaternary nitrogen is a lower alkyl residue, preferably a methyl or ethyl residue or a substituted methyl or ethyl residue, such as for instance, a thiotepa residue. In a preferred embodiment the quaternary chelidonine derivatives are of a nature such as to selectively accumulate in target tissues, particularly cancerous tissues.

In another aspect the invention relates to pharmaceutical compositions containing at least one of the quaternary alkaloid derivatives, particularly quaternary chelidonine derivatives, obtainable in a process according to the present invention.

The invention further relates to the use of the reaction products comprising quaternary alkaloid derivatives as drugs for use in therapeutic applications, and to the use of said derivatives for the manufacture of pharmaceutical compostions for the therapeutic treatment of various diseases or bodily conditions.

Further emodiments of the present invention are laid down in the claims.

DETAILED DESCRIPTION OF THE INVENTION

The process according to the invention comprises reacting an alkaloid or a mixture of alkaloids in an organic solvent with an alkylating agent, preferably with an alkylating agent having itself therapeutic activity, such as for example cytotoxic phosphoramides or phosphoric acid derivatives containing at least one aziridine group, and then washing the reaction products with water. The washing step with water or an equivalent aqueous solvent, e.g. a mild salt solution, facilitates inter alia the subsequent conversion step of the poorly water-soluble or water-insoluble reaction products, i.e. quaternary alkaloid derivatives, into water-soluble compounds, e.g. salts. It is preferred that in case the alkylating agent is a cytotoxic substance it be also water-soluble or at least to decompose upon contact with water into water-soluble components, in order to allow for substantial removal of unreacted alkylating agent or parts thereof from the reaction mixture by the washing step with water.

The washing step with water allows to substantially simplify the manufacturing process since complicated safety precautions owing to the risk of explosion of purely organic solvents, e.g. dimethylether, no longer need to be taken, thus making the process easily upscalable. Moreover, undesired water-soluble components present in the reaction mixture are thereby separated from the reaction products and removed. Surprisingly, it was also found that the washing step has a positive impact on the structure and composition of the reaction products in a way such that the efficiency of the subsequent conversion step of the products into a water-soluble form is augmented by up to 10 to 15 times compared with a process where the washing step is carried out using a purely organic solvent, thus remarkably improving the yield of the desired end product.

The present process can be used, for example, for alkylating reactions of alkaloids with the carcinostatic phosphorus containing compounds mentioned in Claim 1 of AT 377 988, the phosphorus compounds shown in FIG. 3 of the present application being particularly suitable, and most particularly those having an aziridine group.

The term chelidonine as used herein shall refer likewise to either of the members selected from the group consisting of chelidonine, oxychelidonine and methoxychelidonine, unless stated otherwise or unless otherwise derivable implicitly from the description.

A suitable organic solvent according to the present invention is any agent in which the alkaloids intended for the reaction are soluble. The alkaloids can, for example, be dissolved in an organic solvent that facilitates or contributes to the alkylation reaction such as solvent selected from the group consisting of monochloromethane, dichloromethane, trichloromethane, monochloroethane, dichloroethane and trichloroethane.

The alkylating reaction of the alkaloids takes place at elevated temperature, preferably at the boiling point of the solvent.

The resulting reaction product is converted into a water-soluble form after washing with water. This can be carried out according to the process described in AT 377 988 and AT 354 644, by conversion into the water-soluble salts, in particular into the hydrochlorides, for example by passing in a strong acid in liquid or gaseous form such as HCl gas or adding an HCl solution to the organic solution of the washed reaction product, during which or after which the hydrochlorides are precipitated. It appears that by this acidic treatment most of the alkylating agent is split off from an intermediate reaction compound formed between the alkaloids and the alkylating agent, leaving behind modified alkaloid derivatives, wherein the initially tertiary nitrogen atoms have been converted into quaternary nitrogens, wherein to the quaternary nitrogen a hydrogen residue or a residue originating from the alkylating agent is bound as a fourth ligand, the residue preferably being selected from the group consisting of a methyl, ethyl, and tris(1-aziridinyl)phosphine sulphide residue, or from a part of tris(1-aziridinyl)phosphine sulphide. For a better understanding, the subsequent formula (I) illustrates a typical quaternary alkaloid reaction product of the present invention, exemplified with chelidonine:

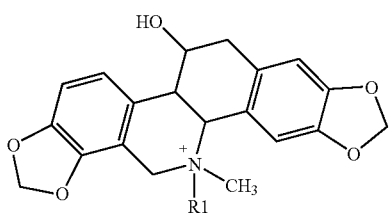

(I)

R1=methyl, ethyl, tris(1-aziridinyl)phosphine sulphide, methyl-R2, ethyl-R2, R2 being a part of tris(1-aziridinyl)phosphine sulphide From an elementary analysis of one of the reaction products precipitated according to the present invention (see Example 3) it appears—without being bound by theory—that at least a part of the alkylating agent or decomposition compounds of the alkylating agent, obtained by the acidic treatment of the reaction mixture after termination of the alkylating, e.g. quaternating reaction, may be occluded to some extent in the crystals of the precipitate or are somehow strongly attached to the crystals, thus withstanding purification of the precipitate by washing with organic solvents such as ether and dichloromethane. Nevertheless it could be proved that the reaction product is still fully functional even in the presence of such accompanying substances.

The water-soluble salt of the reaction product is suitable for application in injection solutions.

In an embodiment of the invention, the reaction is carried out with tris(1-aziridinyl)phosphine sulphide (CAS No. 52-24-4), which in the pharmacopoeia is also known as thiotepa. Further synonyms are ledertepa, Onco thiotepa, TESPA, tespamine, thiophosphamide, thio-TEPA, thiotriethylenephosphoramide, tifosyl, triaziridinylphosphine sulphide, N,N',N''-tri 1,2-ethanediylphosphorothioine triamide; N,N',N''-tri-1,2-ethanediylthiophosphoramide, tri-(ethyleneimino)thiophosphoramide; N,N',N''-triethylenethiophosphoramide, triethylenethiophosphiorotriamide, m-triethylenethiophosphoramide, m-tris(aziridin-1-yl)phosphine sulphide, triethylenethiophosphoramide, tris(1-aziridinyl)phosphine sulphor, tris (ethyleneimino)thiophosphate, TSPA and WR 45312.

In a further embodiment of the invention, an extract of alkaloids, optionally the total alkaloids of *Chelidonium majus* L., in an organic solvent is reacted with tris(1-aziridinyl)phosphine sulphide (thiotepa) and the resulting reaction product, optionally present as a mixture of compounds, is then washed at least once with water. Since thiotepa decomposes in water, the unconverted residue of thiotepa present in excess after the reaction can be removed from the organic phase by this measure. Preferably, the organic solution containing the intermediate reaction product, i.e. the compound formed between alkylating agent and alkaloid, is washed several times and each time is saturated with water. Particularly preferable, the washing is repeated until the excess of highly toxic thiotepa has been completely removed from the reaction product.

In addition, some water-soluble toxic alkaloids which contribute to adverse reactions in medical applications and might even cause cirrhosis of the liver are removed with the aqueous phase from the synthesis mixture or their concentrations are reduced. By means of the Ames test, it was shown that the reaction product of this embodiment, prepared according to the invention, is not mutagenic.

When starting with a total alkaloids extract from *Chelidonium majus* L. the final reaction product is a mixture of alkaloids comprising higher molecular weight reaction products of thiotepa with alkaloids, and of degradation products of thiotepa. As a result of the synthesis process, the solubilities of the alkaloids change. The reaction product consists of a mixture of about 60 to 70% of unreacted *Chelidonium* alkaloids with about 30 to 40% of reaction products of tris(1-aziridinyl)phosphine sulphide.

Tertiary alkaloids represent the main part of the starting components of an alkaloid extract obtained from *Chelidonium majus* L. For example, the following tertiary alkaloids may be contained as starting components in the synthesis mixture: chelidonine, protopin, stylopin, allocryptopin, α-homochelidonine, chelamidine, chelamine, L-sparteine, chelidimerine, dihydrosanguinarine, oxysanguarine, oxychelidonine and methoxychelidonine.

After termination of the alkylating reaction unreacted quaternary alkaloids (e.g. berberine) are substantially removed from the reaction mixture by the washing step with water, while unreacted water-insoluble alkaloids and alyklated alkaloid reaction products remain in the organic solvent. Depending on the nature of the organic solvent and/or of the alkylating agent used for the alkylating reaction, the resulting intermediate reaction product may comprise thiotepa-linked compounds, wherein one thiotepa molecule is linked to one, two or three chelidonine, oxy-chelidonine or methoxy-chelidonine molecules. In addition, it may comprise alkylated alkaloid derivatives, wherein an alkaloid molecule, e.g. a chelidonine, oxy-chelidonine or methoxy-chelidonine molecule, is linked at its quaternary nitrogen to a short chain linear alkyl residue, particularly to a methyl or ethyl group. Still further alkylated reaction compounds may be present in the reaction mixture after termination of the alkylation reaction.

The reaction product obtained from the reaction of the total alkaloids of *Chelidonium majus* L. with thiotepa according to the present invention shows a better spectrum of therapeutic activities than the reaction product obtained from an analogous process where the washing step has been carried out with an organic solvent, e.g. diethylether. At least some compounds present in the reaction product of the present invention, particularly the quaternary chelidonine derivatives, selectively accumulate in cancerous tissues and destroy cancer cells by apoptosis but—in contrast to most known cytostatic agents—without also attacking healthy cells. This results in the good tolerance of a therapy with this preparation and its general suitability for therapeutic and even prophylactic use in individuals at increased risk of developing cancer due to, e.g. hereditary disposition. It is simple to handle and has no significant adverse reactions in therapeutic doses.

The reaction product obtained from the reaction of the total alkaloids of *Chelidonium majus* L. with thiotepa exhibits biological activity in regulation of the metabolism and is suitable for the prevention and therapy of metabolic diseases, such as osteoporosis, but also rheumatic diseases, allergies, viral infections, epilepsy, multiple sclerosis, scars, skin tumours, postoperative wounds and radiation damage.

An extract of the dried roots of *Chelidonium majus* L. may be used as a starting material for the synthesis. The roots have a higher content of alkaloids than the leaves or the stem.

Surprisingly, it was found most recently that when starting with commercially available chelidonine, oxychelidonine or methoxychelidonine as the sole alkaloid source, the resulting reaction product obtained according to the method of the present invention (see for instance Example 3, supra) exhibits therapeutic qualities and activities that are at least comparable to those of the reaction product resulting from the alkylation reaction of total *Chelidonium* alkaloids according to Example 1.

The customary pharmaceutical excipients, in particular for solutions, for example injection or infusion solutions, or for ointment, compress or suspensory bases, are suitable for drugs which contain the reaction products prepared according to the invention.

BRIEF DESCRIPTION OF THE DRAWINGS

FIG. 3 shows selected phosphorus derivatives suitable as reagents.

Figure 1:
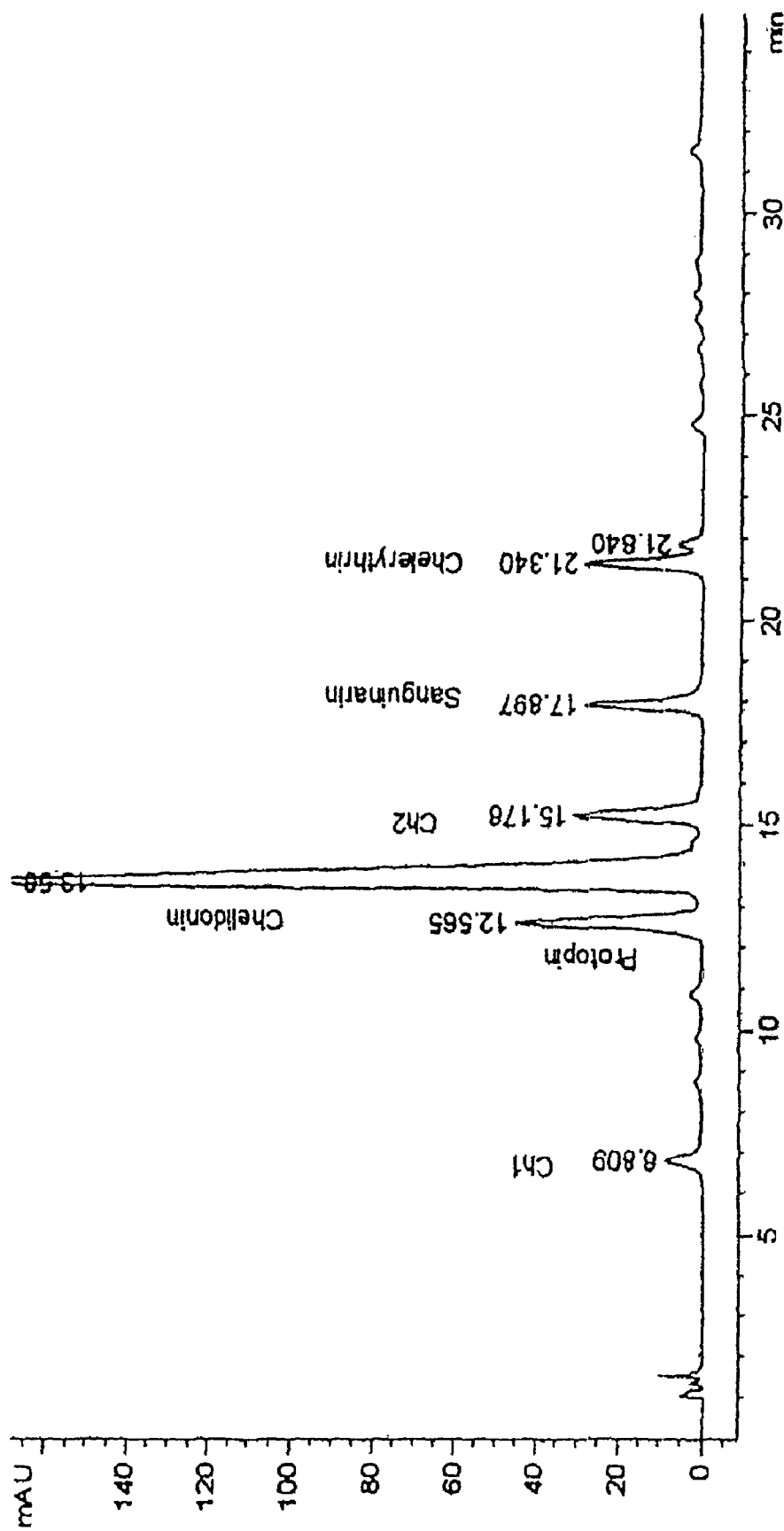
FIG. 1 shows an HPLC diagram with a characteristic total alkaloid composition of the roots of *Chelidonium majus* L.

The following examples are set forth to further illustrate the invention.

EXAMPLE 1

A) Extraction of the Alkaloids:

a. 25 g of an alkaloid salt mixture are suspended in water and transferred to a separating funnel. After the addition of 100 ml of dichloromethane, the separating funnel is shaken. The organic phase is then separated off and is filtered into a glass bottle.

b. 1 N NaOH (pH 8-9) is added to the aqueous phase until turbidity occurs. After the addition of 100 ml of dichloromethane, the mixture is shaken. The organic phase is then separated off and is combined with the dichloromethane phase from step a. This process is repeated, for example 3 times. The organic phases are filtered and combined.

c. The aqueous phase is adjusted to a pH of 10 by adding NaOH. After the addition of dichloromethane, the mixture is shaken. The organic phase is then separated off, filtered and mixed with the other organic phases. The aqueous phase is now adjusted to a pH of 13 with NaOH and the extraction is repeated with dichloromethane.

d. The combined organic phases are evaporated to give an oily, brown material.

B) Reaction with Tris(1-aziridinyl)phosphine Sulphide:

The alkaloid residue is dissolved in dichloromethane, and tris(1-aziridinyl)phosphine sulphide is added. The mixture is refluxed at 80° C. for 2 hours. After cooling to room temperature, the reaction mixture is clarified. Filtration is then carried out and the filtrate is washed several times, for example 3 times or more, with 250 ml of water in a separating funnel.

C) Reaction with HCl

The washed solution is transferred to a glass beaker, stirred and saturated with HCl gas, a hydrochloride complex being precipitated. The precipitated product is filtered off and is washed with diethyl ether, dried and then dissolved in water.

In rats, an $LD_{50}$ value of 485 mg/kg was determined from the reaction product according to Example 1. Studies in mice and rats showed that the product according to the invention modulates the hormone regulation of the thymus and induces the synthesis of substances having thymosin-like activity in animals whose thymus has been removed. This effect is dose-dependent. The preparation increases the number of T-lymphocytes in the peripheral blood by up to 50% ($4.04 \pm 0.43 \times 10^9/l$ before the treatment, $6.24 \pm 0.73 \times 10^9/l$ after the treatment), modulates the humoral immune response to penetrating antigen and the natural killer cell activity of the spleen cells ($198.20 \pm 17.69\%$ compared with $71.50 \pm 9.10\%$ in the control group) and enhances the interferon liberation potential of the white blood corpuscles in animal experiments. The results of the animal experiments are confirmed by clinical observations. Thus, the improvement in the immune parameters was also observed in cancer patients.

Doses of about 5 mg of the preparation from Example 1 per 70 kg body weight can be used for prophylactic and immunological applications. For cancer treatment, 5 mg of the preparation per 20 kg body weight are preferably administered.

EXAMPLE 2

HPLC Fingerprints

Figure 2:
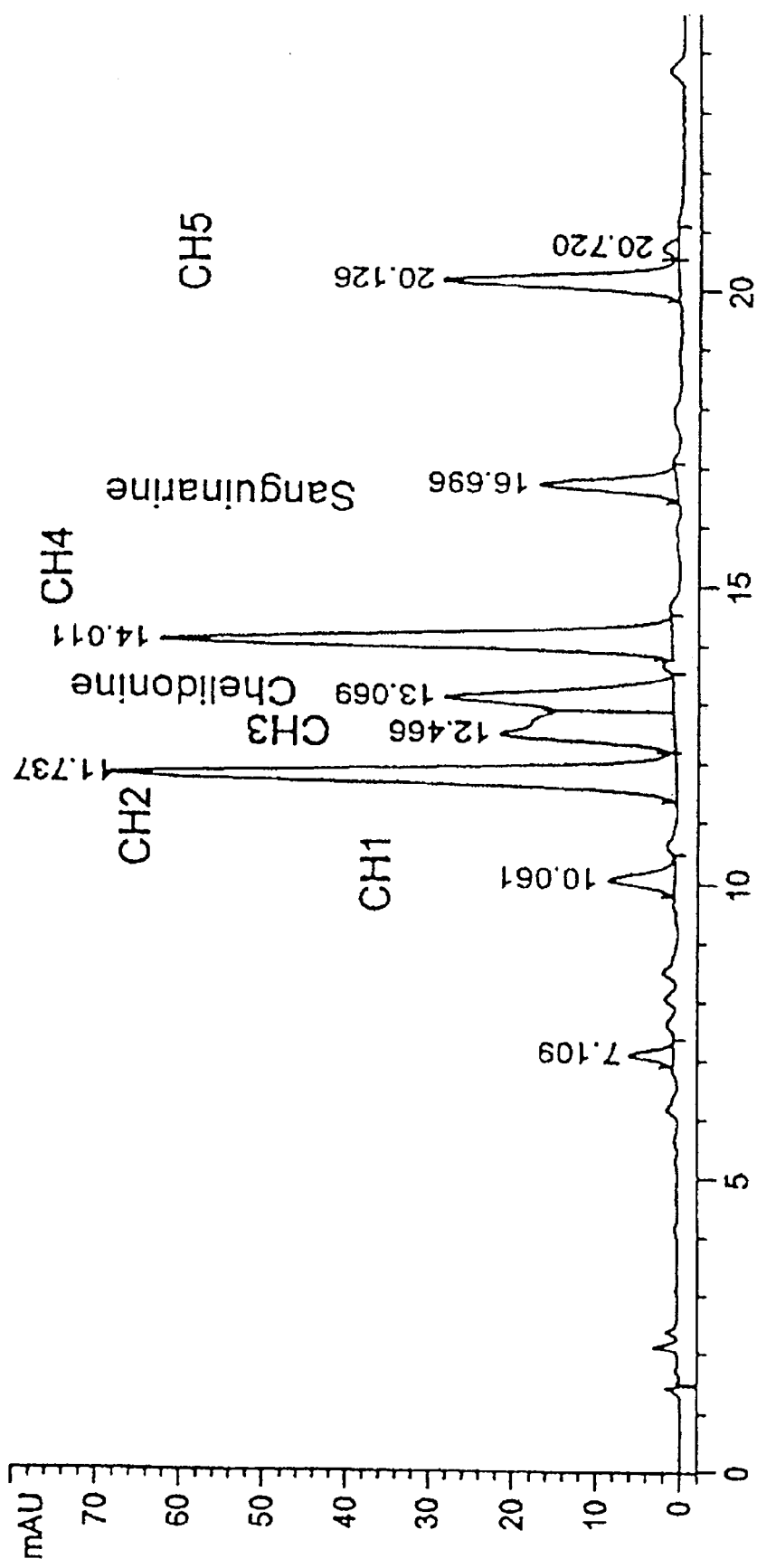
FIG. 2 shows the HPLC fingerprint of a preparation according to Example 1.

The determination was carried out by ion pair reverse-phase chromatography in the gradient mode and with spectral measurement using a DAD detector at 285 nm. At the same time, chromatograms were prepared using reference alkaloids. In addition, an HPLC-MSD analysis was carried out, which showed that there were no peaks apart from those of the alkaloids. The HPLC diagrams of FIGS. 1 and 2 were obtained on the basis of the following experimental data:

Chromatography Parameters:

Column: LiChrospher 60 RP Select B, 5 μm, 125×24 mm ID

Eluent: A) 200 ml (acetonitrile)+800 ml (water)+1.5 g (hexanesulphonic acid)+0.3 ml (85% phosphoric acid) B) 900 ml (acetonitrile)+100 ml (water)+1.5 g (hexanesulphonic acid)+0.3 ml (85% phosphoric acid)

Gradient: 5 min isocratically 100% A;
up to 40% B in 24 min
up to 100% B in 1 min
5 min 100% B;
5 min equilibration with 100% A
Detection: UV light at 285 nm
Eluate flow rate: 1 ml/min, stop after 35 min.
Injected volume: 10 μl Sample Preparation:

Extract before reaction (FIG. 1): 25 mg of alkaloids are dissolved in 40 ml of methanol by ultrasonics, made up to 50 ml and filtered through a membrane filter.

Reaction product (FIG. 2): The reaction product is converted into the hydrochloride salt, dissolved in water in a concentration of 1 mg/ml and adjusted to a pH of between 2.5 and 6.5.

EXAMPLE 3

Figure 4:
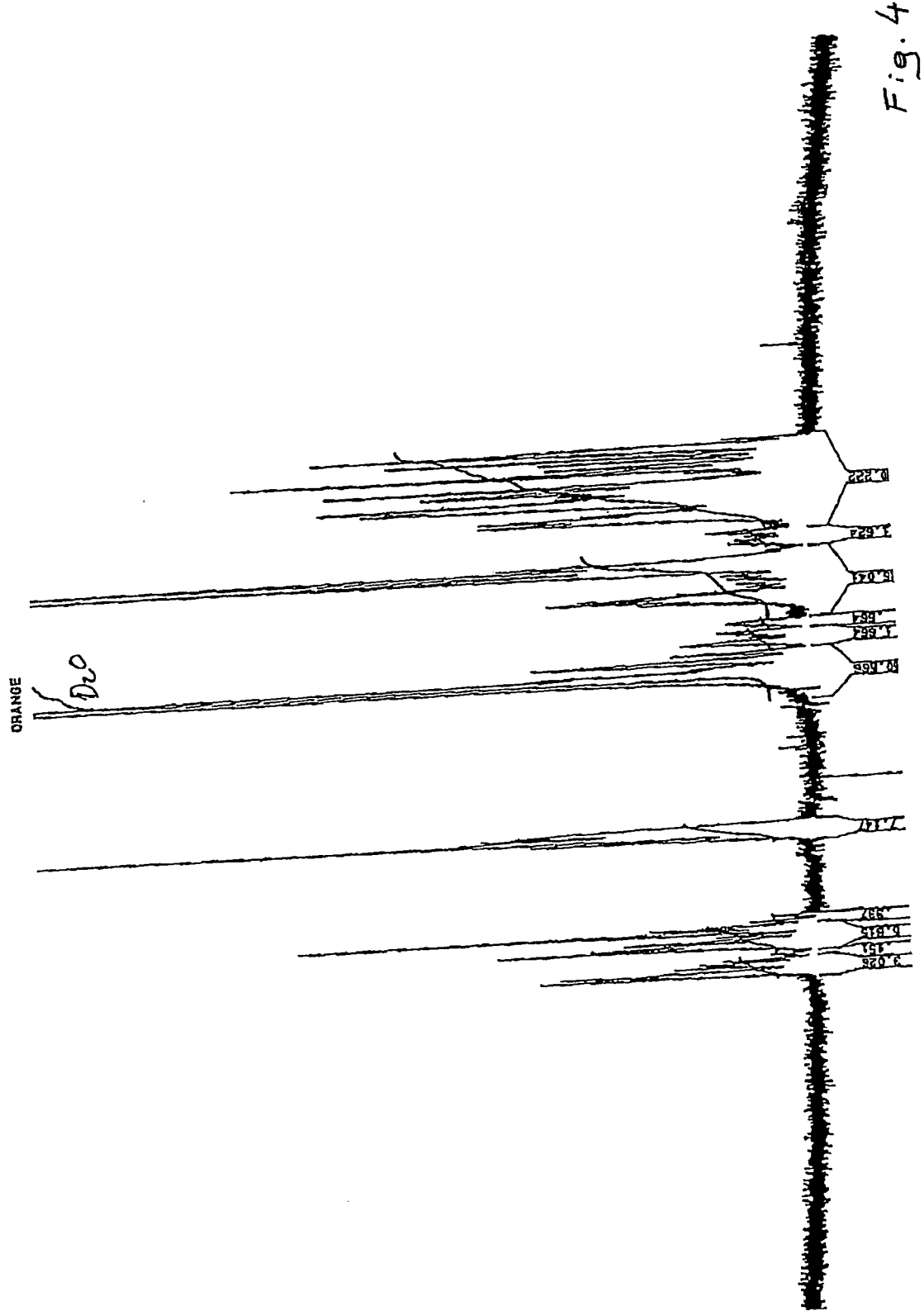
FIG. 4 shows a nuclear magnetic resonance spectrum of the reaction product U-KRS.
Figure 5:
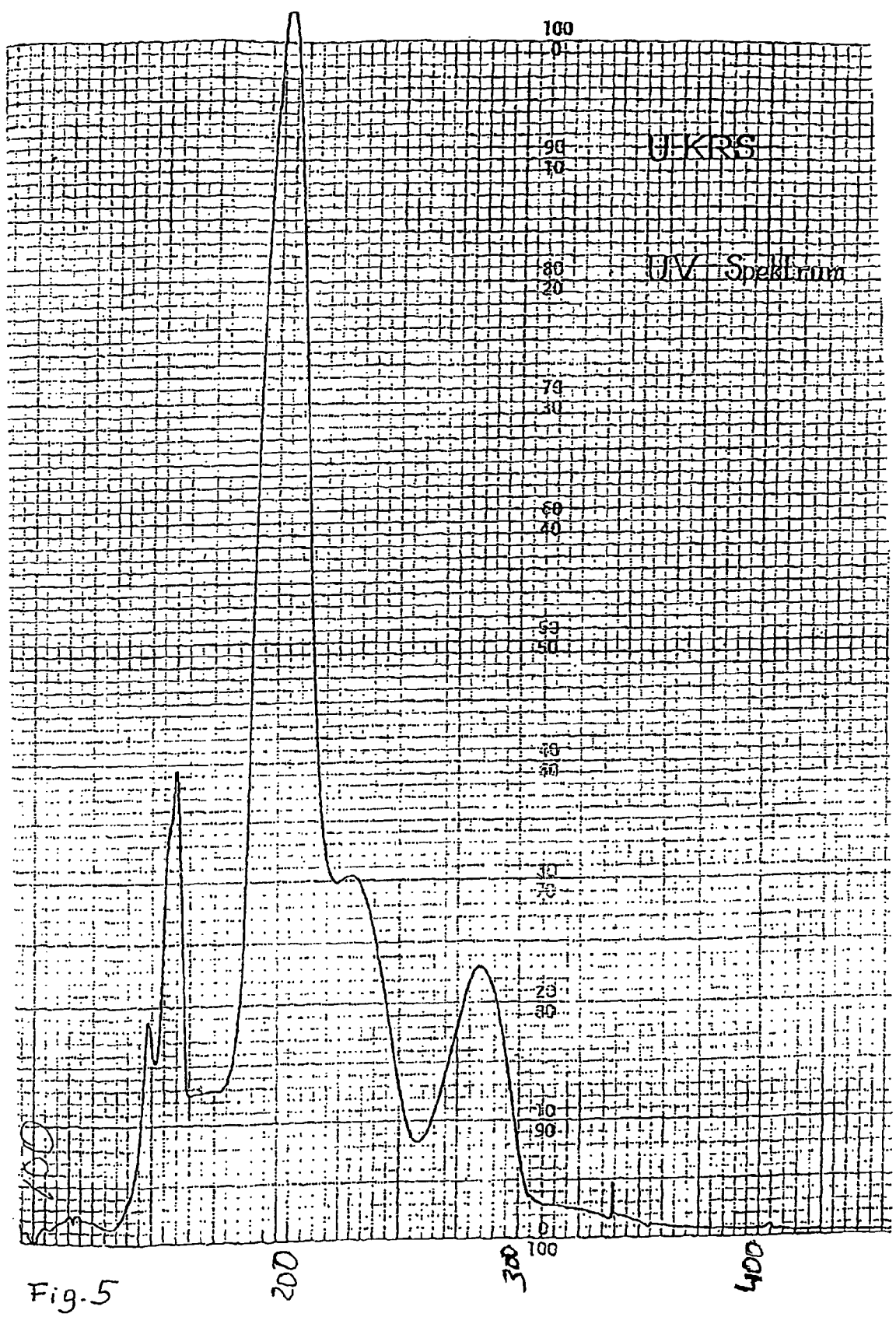
FIG. 5 shows a UV spectrum of the reaction product U-KRS.
Figure 6:
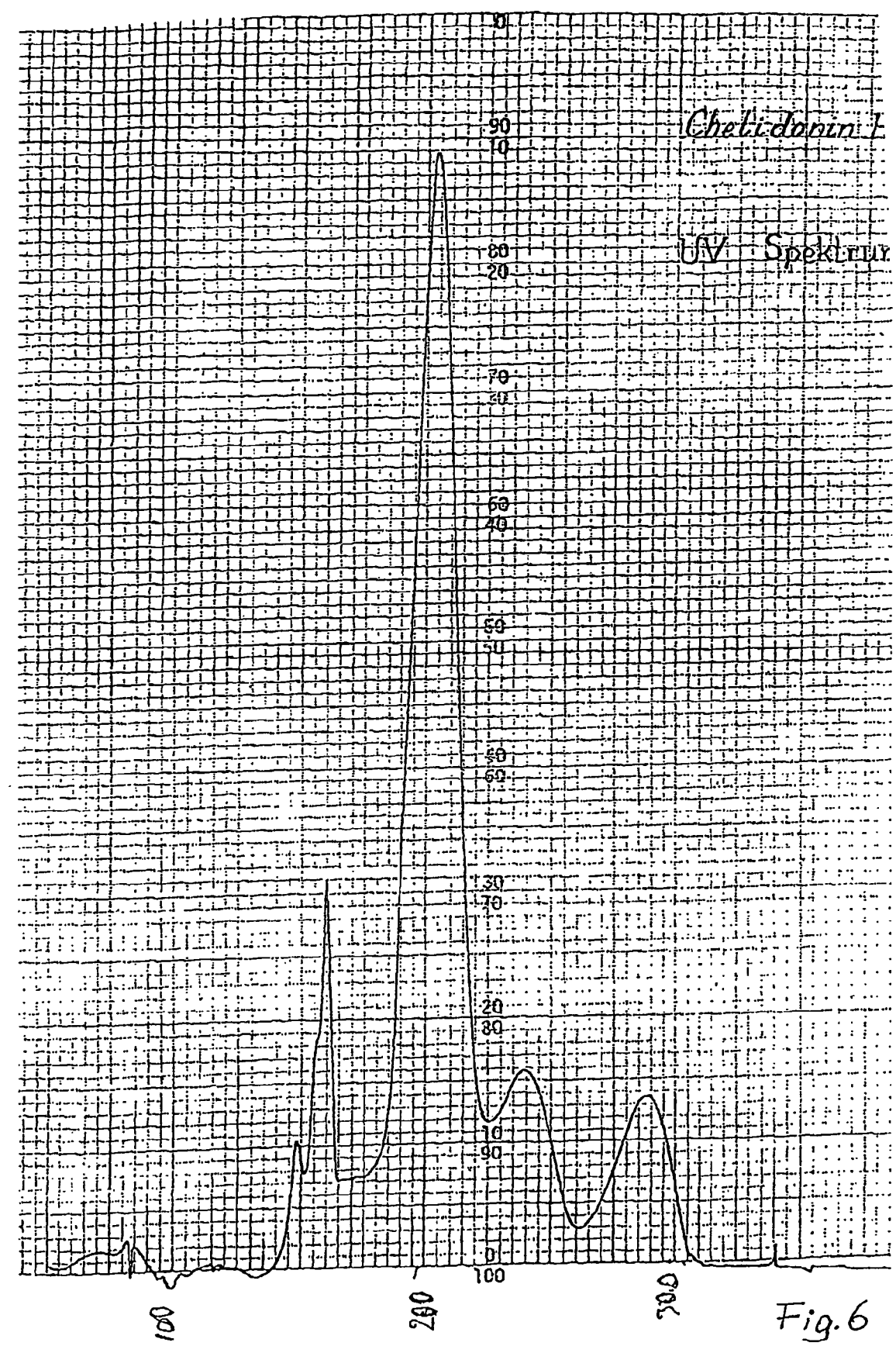
FIG. 6 shows a UV spectrum of chelidonine hydrochloride.

Commercially available, purified chelidonine (Sigma) was subjected to reaction with tris(1-aziridinyl)phosphine sulphide (=thiotepa) according to the conditions described in Example 1. After termination of the alkylation reaction, the subsequent washing step and the conversion step using HCl gas, the final product was further processed as follows:

340 g of the HCl-treated hence water-soluble reaction product were dissolved in water and concentrated close to saturation and allowed to rest in a refrigerator at 8° C. After some hours, spontaneous precipitation occurred and 264 mg precipitate (hereinafter termed U-KRS) was collected. The precipitate comprised slightly yellowish hygroskopic crystals having a rather narrow melting point of 205-207° C. (indicating a fairly well crystallized product) and exhibiting light-blue fluorescence upon irradiation with UV-light at 366 nm. Traces of yellow, orange and red fluorescent bands were also visible. The product did not move when subjected to thin layer chromatography but remained at the starting position ($R_f$=0), except for the traces which at least moved to give an $R_f$>0.1. From the nuclear magnetic resonance (NMR) spectrum (FIG. 4) it gets clear that U-KRS contains aromatic rings comparable to those contained in the chelidonine molecule. The UV spectrum (FIG. 5) exhibits absorption maxima at 148, 155, 160, 205, 230 and 282 nm, very much like the UV spectrum of chelidonine (FIG. 6), which differs therefrom solely in that the peak at 230 nm of U-KRS occurs at 240 nm with chelidonine. This indicates that the nitrogen in U-KRS is quaternary, while in chelidonine it is tertiary.

Figure 7:
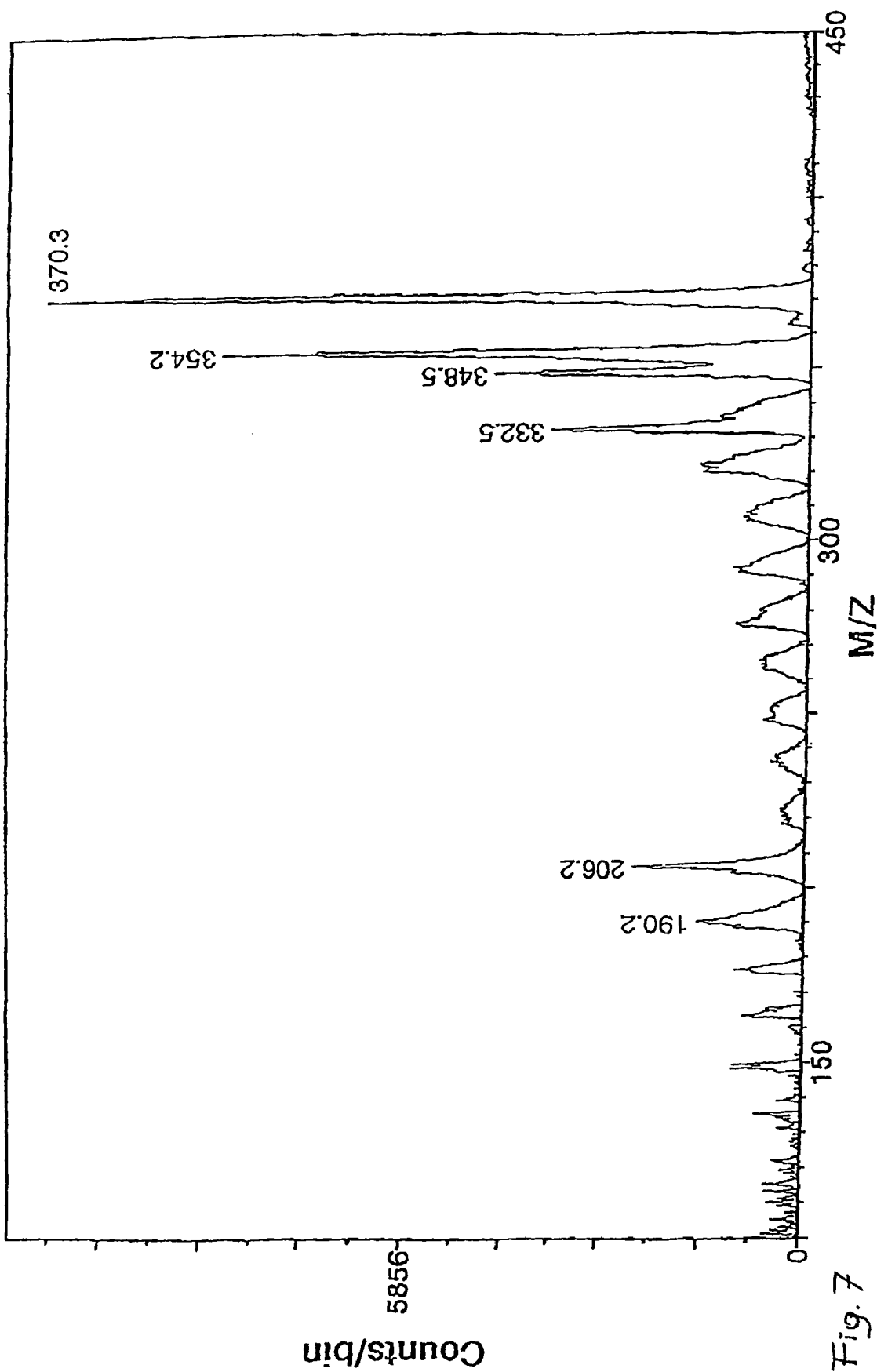
FIG. 7 shows a first section of a mass spectrum of the reaction product U-KRS.
Figure 8:
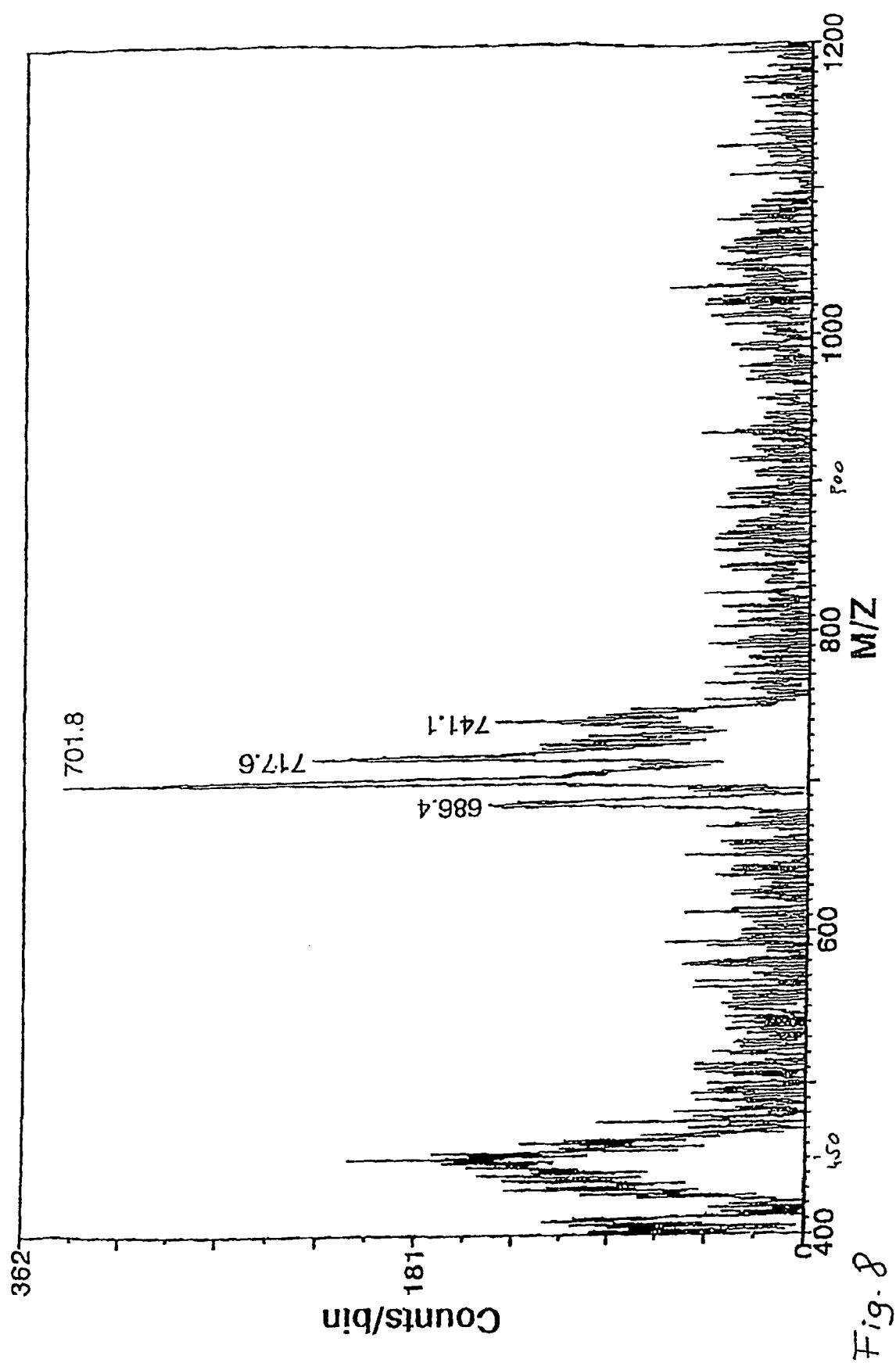
FIG. 8 shows a second section of a mass spectrum of the reaction product U-KRS at a higher resolution.
Figure 9:
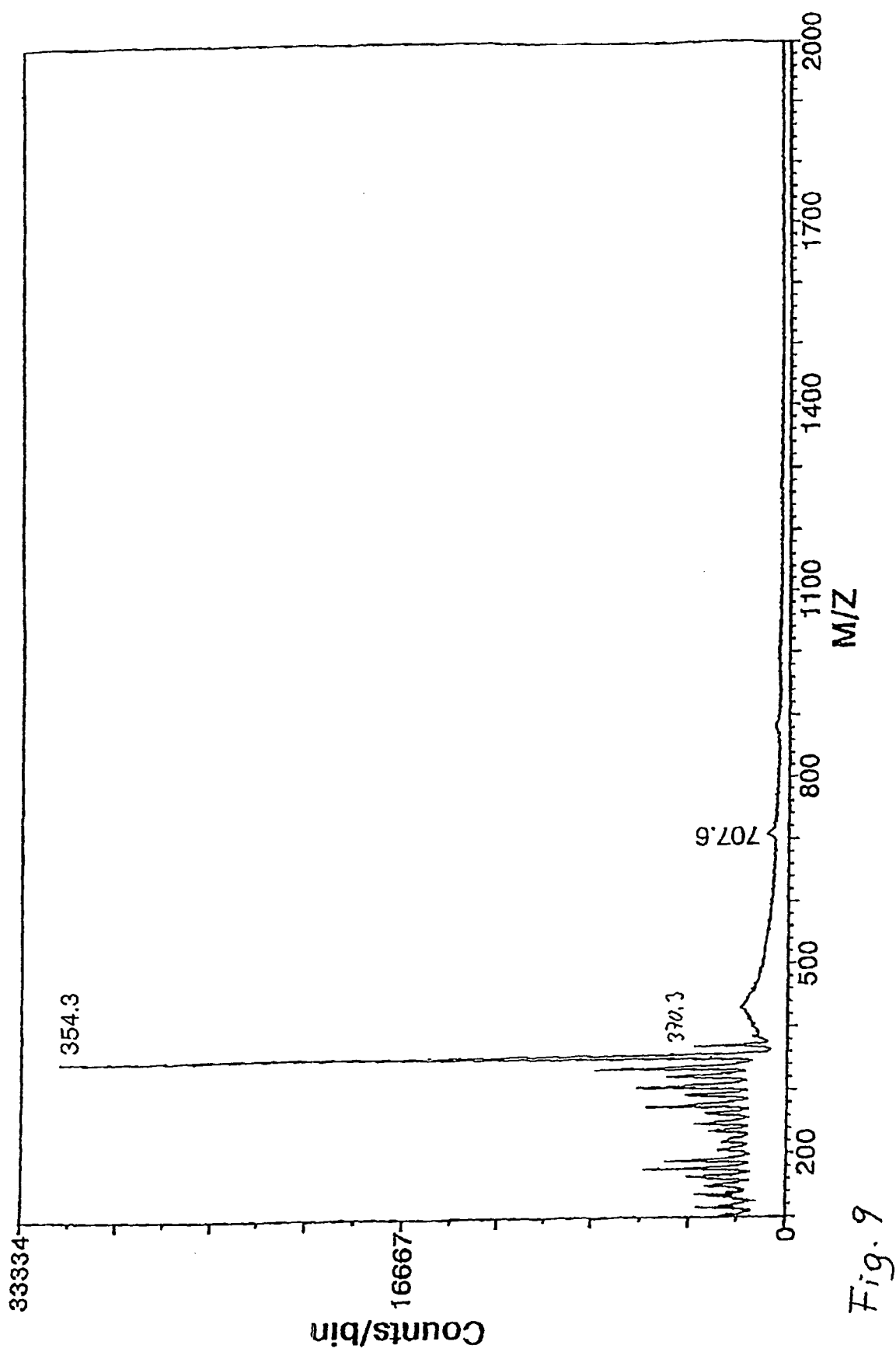
FIG. 9 shows a mass spectrum of chelidonine hydrochloride.

Further analytical details can be derived from the mass spectrograms presented in FIG. 7 and FIG. 8 (U-KRS) and FIG. 9 (chelidonine), and from the result of an elementary analysis of U-KRS revealing the following composition of matter (Tab. 1):

TABLE 1

Elementary composition of U-KRS in % of total mass

| Element | % of total mass |
|---|---|
| C | 45.70 |
|   | 45.05 |
| H | 5.84 |
| N | 6.56 |
|   | 6.37 |
| O | 22.25 |
|   | 19.6 |
| P | 3.27 |
|   | 3.27 |
| S | 2.78 |
|   | 3.06 |
| Cl | 17.29 |

The following examples show various applications of the compound U-KRS resulting from the procedure described in Example 3.

EXAMPLE 4

Selective Inhibition of in vitro Cell Growth by the Anti-tumor Drug U-KRS

Materials and Methods

Cell culture was performed in Roux bottles at 37-37.5° C. in a humidified atmosphere containing 8% CO2. Confluent cultures were detached by a solution of 0.01% trypsin and 0.2% EDTA in phosphate buffered saline (PBS) and split in a ratio ranging from 1:5 to 1:25.

Human endothelial cells were isolated from umbilical veins by collagenase treatment. The culture medium for endothelial cells was M199 supplemented with 15% heat inactivated fetal calf serum, 200 μg/ml endothelial cell growth factor and 90 μg/ml heparin Fluorescence Microscopy Cells were grown in 35 mm dishes and incubated with 100 μg/ml U-KRS for 30-60 min. The culture medium was aspirated, the cells were washed twice with PBS. Coverslips were mounted on the cells and fluorescence was excited using a confocal laser scanning microscope equipped with an argon laser source. The emitted light was detected in a photomultiplier channel. The signals were imaged on a video monitor using the MRC 600 image processing software.

Results

1. In a range from 20-40 μg/ml U-KRS about 55% inhibition of cell growth with endothelial cells was measured. This concentration killed the human osteosarcoma cell line. Hybrids of the two cell types showed nearly the same sensitivity as normal cells.

2. Because of its autofluorescence U-KRS can be detected intracellulary. A laser scanning microscope showed a high uptake of U-KRS in malignant cells.

EXAMPLE 5

U-KRS as Anticancer Agent—Oxygen Consumption

Materials and Methods

In vivo experiments in mice. Two to five control animals were each injected with 50 μl of an Ehrlich mouse ascites tumour suspension i.p. which was 8 d old, freshly taken from a fully grown donor animal. The control group was not further treated. Test group was injected with 10 mg U-KRS/kg animal weight in the abdominal area immediately after the tumour implantation.

Results

Mice implanted with the ascites tumour, either after intraperitoneal or after subcutaneous administration of U-KRS showed a longer survival time than the implant animals which were not otherwise treated.

The measurement of oxygen consumption of an ascites tumour suspension by means of an electrode in vitro brought about a brief increase in consumption after the addition of U-KRS, followed however, by a rapid drop different from that of the control suspension not mixed with U-KRS

EXAMPLE 6

Modification of Antinociceptive Action of Morphine by U-KRS in Rodents

Materials and Methods

Animals: Experiments were performed on male Albino Swiss mice and male Wistar rats.

Treatment: U-KRS was given i.p. in doses starting from 20 mg/kg for mice and 25 mg/kg for rats.

Experimental procedures: In each experiment the four groups of animals were injected with 1) placebo, 2) morphine, 3) U-KRS, 4) U-KRS and morphine.

Results:

The results indicated that simultaneous administration of U-KRS and morphine modified the action of the narcotic analgesic drug. They produced antinociceptive action in the tail-flick test in rats, evident as an increase in the latency time.

The present results show that U-KRS given simultaneously with morphine changes susceptibility of experimental animals to nociceptive reaction in the described tests. The present results suggest that U-KRS can interact with analgesic drugs which are used in cancer.

EXAMPLE 7

Induction of Bimodal Programmed Cell Death in Malignant Cells by the Derivative U-KRS Material and Methods The K562 erythroleukaemia cell line was used, and U-KRS produced in pure crystallized form and dissolved in water at a concentration of 1.2 mg/ml.

The DNA content of K562 cells exposed to various concentrations of U-KRS were analysed using propidium iodide and flow cytometry.

Results

The results of this study show that U-KRS induces bimodal cell death programmes, the first of which, apoptosis, is mediated by quinidine sensitive $Ca^{2+}$-dependent $K^+$ channels; the second modality, blister cell death, is mediated by preventing microtubule formation and thus inducing polyploidy.

EXAMPLE 8

Influence of U-KRS on DNA, RNA and Protein Synthesis in Malignant Cells

Material and Methods $^3$H labelled thymidine, 0.5 µCi in 20 µl medium; uridine, 0.5 µCi in 20 µl medium and leucine, 1.0 µCi in 20 µl medium were placed for 2-4 h into four wells with different U-KRS concentration. Prior to that, the cell lines, guinea pig hepatocydes, C1L hepatocydes, human tonsil cells, murine lymphomas, murine myeloma, Yoshida cells, two HeLa strains, EsB-, EB, lymphomas, ZAC/1, P815 were grown 24H at 37° C. in 96 microtiter wells.

WiDr cells were incubated in a somewhat different schema for 6 and 24 h at U-KRS concentrations of 1, 4, 8 and 14 µg/ml U-KRS.

Results

Fluorometric evaluations show stronger affinity of U-KRS to elements of the cancer cell nucleus that to other cancer cell areas. Fluorescence phenomena may clearly show the strong and the strong and quick affinity exerted by U-KRS in tumour and metastasis areas. No toxic effects are seen in normal cells treated in dosis which are 100 percent growth inhibitory to cancer cell lines tested to date.

EXAMPLE 9

Influence of U-KRS on Human Xenografts

Material and Method

Tumour cells were taken from human tumour xenografts and serially transplanted into nude mice. These cells were used in a colony-forming assay in vitro. Tumour cells were incubated continuously for at least one week with several concentrations of the drug U-KRS. This was done with six different types, and the colony formation was scored for each tumour. The drug effects were reported as percent T/C (Test/Control)

Results

Many different kinds of tumours are sensitive to U-KRS correlating to the variety tested by U-KRS. There the tumouricidal effects seems to be dependent on the regeneration ability of the immune apparatus, which stimulation and modulation may be accomplished by U-KRS.

EXAMPLE 10

Influence of U-KRS on Human Malignant Cell Lines

Material and Methods

Four different malignant cell lines were used: 1) mouse sarcoma; 2) female mammary carcinoma; 3) human colon carcinoma; 4) human melanoma.

U-KRS and PP9AA02 derivatives were added to the culture media.

After irradiation, 200 cells were plated per slide and incubated for one week, then stained and counted.

Results

The results presented here indicated that U-KRS and PP9AA02 derivatives act on human malignant cell lines synergistically as cytoxic substances.

EXAMPLE 11

Induced G2/M Arrest and Apoptosis in Human Epidermoid Carcinoma Cell Lines by U-KRS Material and Methods Primary human keratinocytes were isolated from neonatal skin speciments. Epidermal sheets were trypsinized and single cell suspensions collected by centrifugation.

Results

U-KRS inhibits cell cycle progression in a dose-dependent manner.

U-KRS treatment affects cell cycle distribution and induces apoptosis in A431 and ME180 cells.

Expression of the cyclins, CDKs and CDK inhibitor p27 changes after treatment with U-KRS

EXAMPLE 12

Antimetastatic Effect of U-KRS and its Influence on the Oxygen and Energy Metabolism of Mice With Melanoma B-16

Materials and Methods

The experiment was carried out on 133 C57B/6 male-mice. Metastasizing melanoma B-16 was transplanted to the right shin muscle of each mouse. On the $10^{th}$ day after the tumour transplantation, the animals were divided into two groups. The first group was given U-KRS to sinus venosus of the eye in a dose of 1 mg/kg in the volume of 0.05 ml: 5 injections once in two days. The second group was given sterile physiological solution to sinus venosus in the same regime.

Results

The study was showing that a day after the first intravenous injection on U-KRS the indices of the oxygen regime in the muscular tissue noticeably improved. The rate of $pO_2$ level increased up to the maximum during the oxygen inhalation and the rate of $pO_2$ decreased from the maximum to the initial level after cessation of inhalation. In animals of the experimental group certain indices of the oxidative phosphorylation of the liver mitochonodria also improved a day after the preparation administration. It is known that under progression of the malignant process the oxygen and metabolism is inhibited. In mice which were given 5 injections of U-KRS such inhibition is less pronounced. In the animals of the control group the level of oxygen tention in muscular tissue and the rate of $O_2$ delivery to it were statistically higher. Generalizing the data obtained it is possible to conclude that U-KRS in mice with B/16 melanoma improves the delivery of oxygen to tissues as well as inhibits the destructive effect of the malignant process on the organism bioenergetics.

The subsequent Examples illustrate immuno-modulating and metabolism-regulating properties of U-KRS, rendering U-KRS particularly suitable for the therapeutic treatment of allergic reactions, virus diseases (HIV, Hepatitis A, B and C, E. coli, Influenza), osteoporosis, polyarthritis, psoriasis, and other diseases or bodily conditions.

EXAMPLE 13

Enhancement of Macrophage Tumouricidal Activity by U-KRS

Materials and Methods

BALB/c mice were maintained by brother/sister matings in the laboratory. The tumour D1 DMBA/3 was routinely transplanted in BALB/c by s.c. injection. The tumour became apparent five days after implantation.

In vivo treatment with U-KRS was initiated five days after subcutaneous tumour implantation. Three routs of administration were employed, i.e., intravenous, intraperitonial and subcutaneous. All three experimental groups, of at least 10 mice each, received 5.0 μU-KRS in 0.15 ml of PBS. This dosage was chosen based on preliminary experiments.

Results

The rate of tumour growth in treated mice was significantly diminished. The mice receiving U-KRS did not show any deleterious drug related side effects.

EXAMPLE 14

In vitro Effects of U-KRS on the Phenotype of Normal Human Lymphocytes

Materials and Methods

The study was performed on lymphocytes isolated from peripheral blood of 10 healthy volunteers. The cells were isolated on Ficoll-Paque density gradient centrifugation. Viability of cells was determined by 0.1% trypan blue staining, and found to be 95%.

Lymphocyte subpopulation were quantitated by immunofluorescence using monoclonal antibodies against total T-cells, T-helper cells and T-suppressor cells. Subsequently, cells were treated with FITC/conjugated rabbit F/ab/2 fragments anti-mouse IgG, washed in PBS and mounted on slides using polyvinyl-alcohol and glycerol. In control preparations, PBS or normal mouse serum was used instead of monoclonal antibodies.

Results

The present study indicating the possibility of direct influence of U-KRS on T-cell subpopulations confirmed the earlier observations that U-KRS could be a good immunostimulator of cellular immunity in cancer patients.

EXAMPLE 15

Mitogenic Properties of U-KRS on Human Peripheral Blood Monocytes

Material and Methods

Peripheral blood mononuclear cells. The blood was diluted with an equal volume of PBS containing 1 mM EDTA, pH 7.5, and was layered over Histopaque 1077. The tubes were centrifuged at 2000 rmp for 30 min. The interface layers containing lymphocytes were collected and washed three times with RPMI tissue culture medium Results It was found that even a short period of pre-treatment of the cell with U-KRS had a potent synergic effect on PHA mitogenesis resulting in significantly higher cell stimulation indices than those of PHA alone. Moreover it was found that a short period of PHA treatment of the cells is almost imperative for U-KRS to exert its mitogenic effects.

This study is showing a significant increase in circulating lymphocytes in patients in advanced stages of malignancies treated with U-KRS.

EXAMPLE 16

Modulation of Immune Effector Cell Cytolytic Activity and Tumour Growth Inhibition in vivo by U-KRS Material and Methods Tumour cells: mastocytoma P815 and the AKR leukaemia AKIL cell lines were maintained in DMEM medium supplemented with 9.0% bovine fetal calf serum containing penicillin and streptomycin.

Results

The present in vitro study demonstrates that U-KRS. is an effective biological response modifier augmenting, by up to 48-fold, the lytic activity of splenic lymphocytes obtained from alloimmunized mice. The lytic activities of IL-2 treated spleen cells and peritoneal exudate lymphocytes were also significantly increased by the addition of U-KRS to the cell mediated lysis assay medium.

The results, taken in conjunction that U-KRS also enhances the cytolytic activity of spleen lyphocytes, indicate that the therapeutic effect of U-KRS observed in vivo is mediated by stimulating immune effector cell cytolytic activity.

EXAMPLE 17

Influence of U-KRS on Immunological Blood Parameters in vitro and in vivo

Materials and Methods

96 Wistar rats were used for this study. The initial age was 16 weeks for both male and female rats.

U-KRS and PHA were tested in a #Hthymidine test on T lyphocytes to evaluate the stimulation index in doses from 0.01 to 20 µg/ml.

Results

U-KRS stimulates different subsets of the haematopoietic and immunological systems. In this experiment reticulocytosis is induced as a possible sign of stimulation of certain stem cells or of general activation of the erythropoietic system. As no changes in the absolute leucocyte counts could be demonstrated, it may be postulated that by the action of U-KRS only strong modulating properties, e.g., a dislocation of the different subsets, happened in this experiment.

Stimulation comparable to that gained in these experiments was seen in vitro, including apoptosis in cancer cells.

EXAMPLE 18

Inhibitory Effect of U-KRS on Ovalbumin Antigenicity and Antiovalbumin IgE Antibody Response in Mice Material and Methods The ability of U-KRS to inhibit ovalbumin-induced sensitization was tested in BALB/c and F1 (BALB/c×C57BI/6J) mice. U-KRS was introduced into the mice in the mixture with antigen (ovalbumin) and adjuvant (alum) inhibited the sensitization of mice, reflected in lower anti-OA IgE antibody response and decreased antigen-induced histamine release from mast cells isolated from peritoneal cavities of sensitized mice. The effect of U-KRS on the antigenicity od ovalbumin (OA) in anaphylaxis was tested in heterologous passive cutaneus anaphylactic (PCA) reaction on rats.

Results

The results show that the OA prepared in the mixture with U-KRS had a decreased ability to react with anti-OA IgE antibodies raised against native OA in mice and fixed on the surface of rat mast cells in heterologous PCA reactions. The results suggest that U-KRS pre-treatment of OA may affect its antigenic property and the ability to react with anti-OA IgE antibodies raised against the native IgE molecules.

EXAMPLE 19

Effect of Treatment with U-KRS on Early Osteoporosis

Materials and Methods

U-KRS was administered intraperitoneally in a dose of 30 mg/kg every other day for six months to female rats with ovariectomy-induced early osteoporosis. Administration of U-KRS was started on the second day after the surgical operation. At the end of the long-term treatment with U-KRS each rat was tested for the strength of both humeri and some parameters of rat femur were measured.

Results

The results show that the decrease in the mechanical strength of the humeral bones and some changes in the femur caused by ovariectomy were prevented by the six-month treatment with U-KRS.

EXAMPLE 20

Influence of U-KRS Preparation on Influenza Viruses and the Bacteria E. coli and S. aureus Material and Methods Influenza viruses of the APR8/HON1/34 strain were cultured on 10-day-old hen embryos;

E. coli bacteria derived from current clinical material and the strain 209P of S. aureus were employed. U-KRS preparation of the series 290614.

Results

This study confirms the existing of anti-infectious action of U-KRS preparation in the infected macro organism. This influence is exerted through the stimulation of some elements of the host immune system due to a secondary destruction of micro organisms or cells infected by these micro organisms.

EXAMPLE 21

Biological Activity of U-KRS with Respect to Influenza Virus

Material and Methods

Virus of A type, Port-Chalmers 1/73 culture, antigenic $H_3N_2$ variety. The virus was injected at 1, 10 and 100 $EID_{50}$ per embryo. U-KRS was dissolved de novo in Hanks solution.

Results

It was confirmed that U-KRS has the hampering action upon the development of the infective process.

EXAMPLE 22

Action of U-KRS on Effects of Irradiation

Materials and Methods

CBA/J male mice of 16/20 g body weight.

Short-term whole-body gamma-irradiation of mice at doses ranging from 6.0 Gy to 7.5 Gy was performed. Long-term irradiation with the cumulative dose of 8.75 Gy was performed using the CEGO device.

U-KRS was administered intraperitonially at doses of 0.1, 1.4 and 12 mg/kg body weight.

Results

The ability of U-KRS to modify the effects of irradiation was studied in CBA/J mice using the dosage of the drug from 0.1 to 12 mg/kg. U-KRS was found to increase the survival rate of mice by 50-60% at irradiation dosis from 5.00 to 7 Gy with no effect at the dose of 7.5 Gy. Varying the dosage of the drug did not influence the outcome of irradiation.

The main outcome of the present study is the finding that U-KRS is capable of modifying the effects of irradiation when applied in both prophylactic and curative regimes.

EXAMPLE 23

Effects of U-KRS Against Ionizing Radiation

Materials and Methods

Brest carcinoma, colorectal adenocarcinomas, glioblastoma and pancreas adenocarcinomas cell lines. U-KRS preparation.

The effect of U-KRS on cell survival was tested at concentration ranging FROM 0.2 μG ML. The exposure times were 1, 3 and 24 h, after which the cells were washed with phosphate/buffered saline and fresh medium was added.

Results

U-KRS treatment resulted in differential time- and dose-dependent reduction in clonogenic cell survival. All four human tumour cell lines tested showed different sensitivities towards U-KRS with an up to 100-fold higher reduction of clonogenic survival as compared with human fibroblasts for 24 h incubation.

The invention claimed is:

1. A process for the manufacture of a chelidonine reaction product having a quaternary nitrogen according to formula (I), wherein R1 is a hydrogen, or a methyl or ethyl residue and wherein the chelidonine reaction product is present in water-soluble form as a salt of a strong acid,

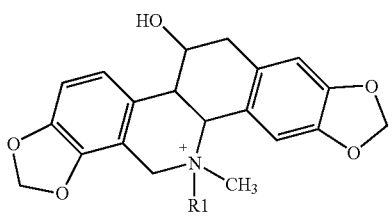

the process comprising:
 a) providing a reaction mixture comprising an organic solvent, an alkaloid which is chelidonine, and an alkylating agent, and carrying out an alkylation reaction by reacting the chelidonine with the alkylating agent in the presence of the organic solvent, so as to form a chelidonine reaction product having a quaternary nitrogen;
 b) after termination of the alkylation reaction, subjecting the resulting reaction mixture to at least one washing step with an aqueous solvent or water, to remove water-soluble compounds present in the reaction mixture; and
 c) subjecting the washed reaction mixture to a treatment with a strong acid in gaseous or liquid form, thereby converting the quaternary chelidonine reaction product in the reaction mixture into a water-soluble salt.

2. The process according to claim 1, wherein in step c) the washed reaction mixture is subjected to a treatment with gaseous hydrogen chloride or a hydrogen chloride solution.

3. The process according to claim 1, wherein in step c) the reaction product precipitates during or after the treatment with acid, whereafter the precipitate is separated from the organic solvent, and optionally further purified using organic solvents.

4. The process according to claim 1, wherein the alkylation reaction is carried out at elevated temperature.

5. The process according to claim 4, wherein the alkylation reaction is carried out at the boiling point of the solvent.

6. The process according to claim 1, wherein the alkylating agent is a physiologically active agent.

7. The process according to claim 6, wherein the alkylating agent is a cytotoxic agent.

8. The process according to claim 1, wherein the alkylating agent is water-soluble or decomposes into water-soluble components upon contact with water.

9. The process according to claim 1, wherein the organic solvent is selected from the group consisting of monochloromethane, dichloromethane, trichloromethane, monochloroethane, dichloroethane and trichloroethane.

10. The process according to claim 1, wherein the alkylating agent is tris(1-aziridinyl)phosphine sulphide (CAS 52-24-4).

11. An alkaloid reaction product comprising a chelidonine reaction product having a quaternary nitrogen according to formula (I), wherein R1 is a hydrogen, or a methyl or ethyl residue

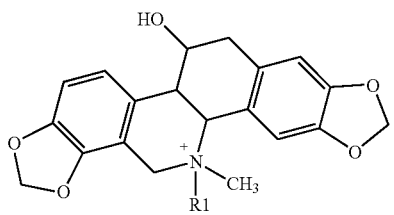

wherein the chelidonine reaction product is present in water-soluble form as a salt of a strong acid and wherein the alkaloid reaction product is useful as a drug or medicament.

12. The alkaloid reaction product according to claim 11, obtained by a process comprising:
 a) providing a reaction mixture comprising an organic solvent, an alkaloid which is chelidonine, and an alkylating agent, and carrying out an alkylation reaction by reacting the chelidonine with the alkylating agent in the presence of the organic solvent, so as to form a chelidonine reaction product having a quaternary nitrogen;
 b) after termination of the alkylation reaction, subjecting the resulting reaction mixture to at least one washing step with an aqueous solvent or water, to remove water-soluble compounds present in the reaction mixture; and
 c) subjecting the washed reaction mixture to a treatment with a strong acid in gaseous or liquid form, thereby converting the quaternary chelidonine reaction product in the reaction mixture into a water-soluble salt.

13. The alkaloid reaction product according to claim 12, obtained through reaction of chelidonine with an alkylating agent, wherein in the product an initially tertiary nitrogen is present in quaternary form.

14. The alkaloid reaction product according to claim 12, wherein the chelidonine reaction product is present in the form of a hydrochloride.

15. The alkaloid reaction product according to claim 12, wherein the product further comprises at least one compound selected from the group consisting of unreacted tertiary chelidonine, unreacted alkylating agent, and decomposition products of the alkylating agent.

16. A chelidonine reaction product, wherein naturally occurring chelidonine is present in a quaternated form according to formula (I),

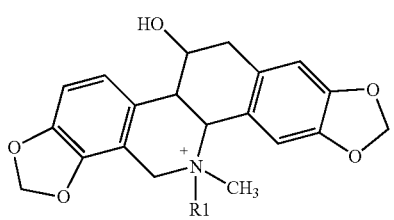

wherein as a fourth ligand R1 to the quaternary nitrogen a hydrogen or a methyl or ethyl residue is present, wherein the chelidonine reaction product is present in water-soluble form as a salt of a strong acid, and wherein the chelidonine reaction product is useful as a drug or a medicament.

17. The chelidonine reaction product according to claim 16 in the form of a hydrochloride.

* * * * *